US006878381B2

(12) United States Patent
Collington

(10) Patent No.: US 6,878,381 B2
(45) Date of Patent: Apr. 12, 2005

(54) RESORCINOL COMPOSITION

(75) Inventor: Eric William Collington, Knebworth (GB)

(73) Assignee: Pfizer, Inc, New York, NY (US)

( * ) Notice: Subject to any disclaimer, the term of this patent is extended or adjusted under 35 U.S.C. 154(b) by 398 days.

(21) Appl. No.: 10/061,040

(22) Filed: Jan. 30, 2002

(65) Prior Publication Data

US 2002/0155075 A1 Oct. 24, 2002

Related U.S. Application Data

(63) Continuation-in-part of application No. 09/525,643, filed on Mar. 15, 2000, now abandoned.
(60) Provisional application No. 60/125,553, filed on Mar. 22, 1999.

(51) Int. Cl.$^7$ .............................. A61K 6/00; A61K 7/00
(52) U.S. Cl. .................................................. 424/401
(58) Field of Search ........................... 424/401, 59, 60, 424/62; 514/730, 731, 732, 844

(56) References Cited

U.S. PATENT DOCUMENTS

| | | | |
|---|---|---|---|
| 3,697,275 | A | 10/1972 | Havakawa |
| 3,756,818 | A | 9/1973 | Hakvakawa et al. |
| 3,933,925 | A | 1/1976 | Greco |
| 4,006,218 | A | 2/1977 | Sipos |
| 4,225,619 | A | 9/1980 | Brickl et al. |
| 4,391,827 | A | 7/1983 | Harbert et al. |
| 5,304,679 | A | 4/1994 | McEvilv et al. |
| 5,399,785 | A | 3/1995 | Miura et al. |
| 5,468,472 | A | 11/1995 | LaGrange et al. |
| 6,132,740 | A | * 10/2000 | Hu .............................. 424/401 |
| 2002/0161041 | A1 | * 10/2002 | Browning et al. .......... 514/489 |

FOREIGN PATENT DOCUMENTS

| | | |
|---|---|---|
| CA | 2094465 | 10/1993 |
| DE | 31 27 590 A1 | 8/1982 |
| DE | 36 04 865 A1 | 8/1987 |
| EP | 0 341 664 | 11/1989 |
| EP | 0 524 439 A1 | 1/1993 |
| EP | 0 551 849 A1 | 7/1993 |
| EP | 0 623 339 A1 | 11/1994 |
| EP | 0 701 988 A1 | 3/1996 |
| EP | 0 904 774 | 3/1999 |
| JP | H2-49715 | 2/1990 |
| JP | 4-169516 | 6/1992 |
| JP | 5-4905 | 1/1993 |
| JP | H6-56641 | 3/1994 |
| WO | 90/13618 | 11/1990 |
| WO | 91/11119 | 8/1991 |

OTHER PUBLICATIONS

Chemical Abstracts, 63:6872g, vol. 63, 1965.
Chemical Abstracts 52:10392a, vol. 52.
Pharmacology, 51:5310e.
Chemical Abstracts, 51:1464h, vol. 51.
Pharmacology, 51:13219b.
Baek, Seung–Hwa, "Simplified Cannabidiols. Part 1. Boron Trifluoride–Diethyl Ether on Alumina: A Modified Lewis Acid Reagent. Friedel–Crafts Alkylation of 5–Alkylresorcinols with Cyclic Allylic Alcohols", J. Chem. Research (S), 1994, pp 451.
Baek, Seung–Hwa, "A Simple One–Step Akylation of Orcinol Derivatives", Bulletin of the Korean Chemical Society, vol. 9, No. 2, 1988; ISSN 0253–2964.
Yusupov, A., et al, "Cyclo–Alkylation of Resorcinol And Its Esters", Reports of the Uzbek SSR Academy of Sciences, 1970, Nr. 6—Translated Copy.
Pisanenko, D.A., et al, "Antimicrobial Activity of Cycloalkenyl– And 4–(a–ARYL Cyclopentyl)–Phenols", Chrenovitskiy Medical Institute, Polytechnic Institute, Nov., 1976—Translated Copy.
Yusupov, A., "Reaction of Resorcinol and its Methyl Esters With Cyclopentene and Cyclohexene", Uzbek SSR Academy of Sciences, 1970, Nr. 5—Translated Copy.
Ardurasuleva, A.R., et al, "Cyclopentylation of Resorcinol and its Esters", Uzbek SSR Academy of Sciences, 1968, Nr. 5—Translated Copy.
Repinskaya, I.B., et al, "Interactin of Phenols and Their Derivatives With Aromatic Compounds in the Presence of Acid Agents", Journal of Organic Chemistry, vol. XVI, Nr. 7, 1980—Translated Copy.
Repinskaya, I.B., et al, "Reaction of Phenols and Their Derivatives with Aromatic Compunds in the Presence of Acidic Agents", Zhurnal Organicheskoi Khimii, vol. 16, No. 7, pp 1508–1514, Jul. '80.
Gottesfield, J.M., "The Inhibition of Deoxyribonuclease I by Hydroxybiphenyls", Biochimica Et Biophysica ACTA, 228 (9171); pp 365–386.
Fujikawa, et al, "Studies on Antiseptics for Foodstuff. LXXIII. Studies on 3–Halogeno–4–hydroxy–benzoic Acid Esters, 4–Alkylresorcinol, 4–Arylresorcinol, 5–Alkyl–2, 4–dihydroxybenzaldehyde,5–Alkyl–chloro–2,4–dihydroxybenzaldehyde, 4–Aryl–6–chloro–resorcinol", Yakujaku Zasshi (1972), 92(6), pp 768–771.
Patent Abstracts of Japan, Publication No. 04169511, Jun. 17, 1992.
Derwent Abstracts, 93–055163, XP–002087694, Jan. 14, 1993.

* cited by examiner

Primary Examiner—Thurman K. Page
Assistant Examiner—Sharon Howard
(74) Attorney, Agent, or Firm—Rosanne Goodman

(57) ABSTRACT

The present invention relates to the use of a resorcinol derivative, i.e., 4-(2,4-dihydroxyphenyl)cyclohexanol, or a pharmaceutically acceptable salt thereof, as a skin lightening agent.

17 Claims, No Drawings

RESORCINOL COMPOSITION

This application is a continuation-in-part of application Ser. No. 09/525,643, filed Mar. 15, 2000 now abandoned, which claims priority from U.S. provisional application No. 60/125,553, filed Mar. 22, 1999, which are incorporated herein by reference.

FIELD OF THE INVENTION

The present invention relates to the use of a resorcinol derivative, i.e., 4-(2,4-dihydroxyphenyl)cyclohexanol or a pharmaceutically acceptable salt thereof, as a skin lightening agent.

BACKGROUND OF THE INVENTION

The terms "lightening agent" and "depigmentation agent" are used interchangeably throughout this document.

Skin color in humans arises from a complex series of cellular processes that are carried out within a unique population of cells called melanocytes. Melanocytes are located in the lower part of the epidermis, and their function is to synthesize a pigment, melanin, which protects the body from the damaging effects of ultraviolet radiation.

When skin is exposed to ultraviolet radiation, such as that contained in sunlight, melanocytes increase their synthesis of melanin. Melanin is deposited in melanosomes, which are vesicles found within the cell. The melanosomes are extruded from the cell and carried to the surface of the skin by keratinocytes, which internalize the melanin containing melanosomes. The end result is that the visible layers of the skin exhibit a brown color typically known as a "tan". The darkness of the color observed in the skin is proportionate to the amount of melanin synthesized by melanocytes and transferred to the keratinocytes.

The mechanism by which skin pigmentation is formed, i.e., melanogenesis, is particularly complex and schematically involves the following main steps: Tyrosine→L-Dopa→Dopaquinone→Dopachrome→Melanins. The first two reactions in this series are catalyzed by the enzyme tyrosinase. The activity of tyrosinase is promoted by the action of α-melanocyte stimulating hormone or UV rays to have melanin eventually formed in the skin. It is well established that a substance has a depigmenting effect if it acts directly on the vitality of the epidermal melanocytes where melanogenesis normally occurs and/or if it interferes with one of the stages in melanin biosynthesis. The active compounds that are employed in the various methods and compositions of this invention inhibit tyrosinase and thus inhibit or decrease melanin biosynthesis.

There is a strong demand for agents that enable acquired deposition sites, such as spots or freckles, to be restored to a normal skin color. For this purpose, a variety of agents and methods have been developed and put on the market. Examples of such methods are (a) a method wherein vitamin C (L-ascorbic acid) having good reducing ability is administered orally in large amounts, (b) a method wherein glutathione is administered parenterally; (c) a method wherein a peroxide, such as hydrogen peroxide, zinc peroxide, sodium peroxide and the like, which is believed to have the bleaching action of melamine, is administered: and (d) a method wherein vitamin C or cysteine is administered topically in the form of an ointment, cream, lotion or the like. Vitamin C has a problem with respect to stability and becomes so unstable in water-containing systems that they will cause changes in odor and color. Thiol compounds such as glutathione and cysteine do not exhibit a satisfactory depigmental effect since the development of the effect is very slow.

The substances in widest use at the present time as depigmentors are, in particular, hydroquinone and its derivatives, particularly its ethers such as hydroquinone monomethyl ether. These compounds, while effective, are known to produce side effects that can be dangerous. Hydroquinone, use of which is limited to a concentration of 2%, is both irritating and cytotoxic to the melanocyte.

U.S. Pat. No. 4,526,179 refers to certain hydroquinone fatty esters that have good activity and are less irritating and more stable than hydroquinone.

Japanese Patent Application No. 27909/86 refers to other hydroquinone derivatives that do not have the drawbacks of hydroquinone but that have relatively poor efficacy.

U.S. Pat. No. 5,449,518 refers to 2,5-dihydoxyphenyl carboxylic acid derivatives as skin depigmentation agents.

European Patent Application EP 341,664A1 refers to certain resorcinol derivatives as tyrosinase inhibitors and skin depigmentation agents.

The use of topical depigmention agents that have good efficacy and are harmless is particularly desirable for treating the following: regional hyperpigmentation caused by melanocytic hyperactivity, such as idiopathic melasma occurring either during pregnancy (mask of pregnancy or chloasma) or secondary to estrogen-progesterone contraception; local hyperpigmentation caused by benign melanocytic hyperactivity and proliferation such as lentigo senilis or liver spots; accidental hyperpigmentation such as postlesional photosensitization and scarring; and certain forms of leukoderma such as vitiligo where, if the injured skin cannot be repigmented, the residual zones of normal skin are depigmented to impart a homogeneous white color to the entire skin.

The compound of formula I, i.e., 4-(2,4-dihydroxyphenyl) cyclohexanol, and its pharmaceutically acceptable salts, which are used in the various methods and compositions of this invention, are useful in the treatment of the foregoing dermatological conditions as well as other dermatological conditions, some of which are referred to later in this document, for which the subject being treated desires, for medicinal or cosmetic purposes, to lighten or reduce the pigmentation of the skin affected by the condition.

4-(2,4-dihydroxyphenyl)cyclohexanol, and its pharmaceutically acceptable salts, are also useful for the treatment of inflammatory disorders such as psoriasis and acne, and for the treatment of dandruff.

SUMMARY OF INVENTION

The invention relates to use of the compound 4-(2,4-dihydroxyphenyl)cyclohexanol, which has the formula:

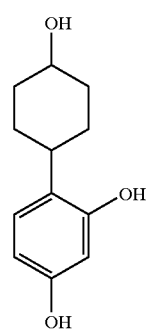

I

The present invention also relates to use of a pharmaceutically acceptable salt of the compound of formula I.

The present invention also relates to a topical pharmaceutical composition for lightening skin or reducing the pigmentation of skin in a human, comprising an amount of the compound of formula I or a pharmaceutically acceptable salt thereof that is effective in lightening skin or reducing the pigmentation of skin, and a pharmaceutically acceptable carrier.

The present invention also relates to a method of lightening skin or reducing the pigmentation of skin in a human, comprising administering to said human an amount of the compound of formula I or a pharmaceutically acceptable salt thereof that is effective in lightening skin or reducing the pigmentation of skin.

The present invention also relates to a topical pharmaceutical composition for inhibiting tyrosinase in a human, comprising a tyrosinase-inhibiting effective amount of the compound of formula I or a pharmaceutically acceptable salt thereof, and a pharmaceutically acceptable carrier.

The present invention also relates to a method of inhibiting tyrosinase in a human, comprising administering to said mammal a tyrosinase-inhibiting effective amount of the compound of formula I or a pharmaceutically acceptable salt thereof.

The present invention also relates to a topical pharmaceutical composition for lightening skin or reducing the pigmentation of skin in a human, comprising a tyrosinase-inhibiting effective amount of the compound of formula I or a pharmaceutically acceptable salt thereof, and a pharmaceutically acceptable carrier.

The present invention also relates to a method of lightening skin or reducing the pigmentation of skin in a human, comprising administering to said human a tyrosinase-inhibiting effective amount of the compound of formula I or a pharmaceutically acceptable salt thereof.

The present invention also relates to a topical or transdermal pharmaceutical composition for the treatment of an inflammatory disorder such as psoriasis, dermatitis or acne, or dandruff, in a human, comprising an amount of the compound of formula I or a pharmaceutically acceptable salt thereof that is effective in treating such disorder or condition, and a pharmaceutically acceptable carrier.

The present invention also relates to a method of treating inflammatory disorders such as psoriasis, dermatitis or acne, or dandruff, in a human, comprising administering to said human an amount of the compound of formula I or a pharmaceutically acceptable salt thereof that is effective in treating such disorder or condition.

The present invention also relates to a topical or transdermal pharmaceutical composition for the treatment of an inflammatory disorder such as psoriasis, dermatitis or acne in a human, comprising a tyrosinase-inhibiting effective amount of the compound of formula I or a pharmaceutically acceptable salt thereof, and a pharmaceutically acceptable carrier.

The present invention also relates to a method of treating inflammatory disorders, such as psoriasis, dermatitis or acne, in a human, comprising administering to said human a tyrosinase-inhibiting effective amount of the compound of formula I or a pharmaceutically acceptable salt thereof.

The compound of formula I, i.e., 4-(2,4-dihydroxyphenyl)cyclohexanol, may exist in different diastereomeric forms. This invention relates to all stereoisomers of 4-(2,41-dihydroxyphenyl)cyclohexanol and mixtures thereof, and to all pharmaceutical compositions and methods of treatment defined above that contain or employ them, respectively.

Formula I includes compounds identical to that depicted above but for the fact that one or more hydrogen, carbon or other atoms are replaced by isotopes thereof. Such compounds may be useful as research and diagnostic tools in metabolism pharmacokinetic studies and in binding assays.

DETAILED DESCRIPTION OF THE INVENTION

The compound of formula I may be prepared as described in the following reaction scheme and discussion.

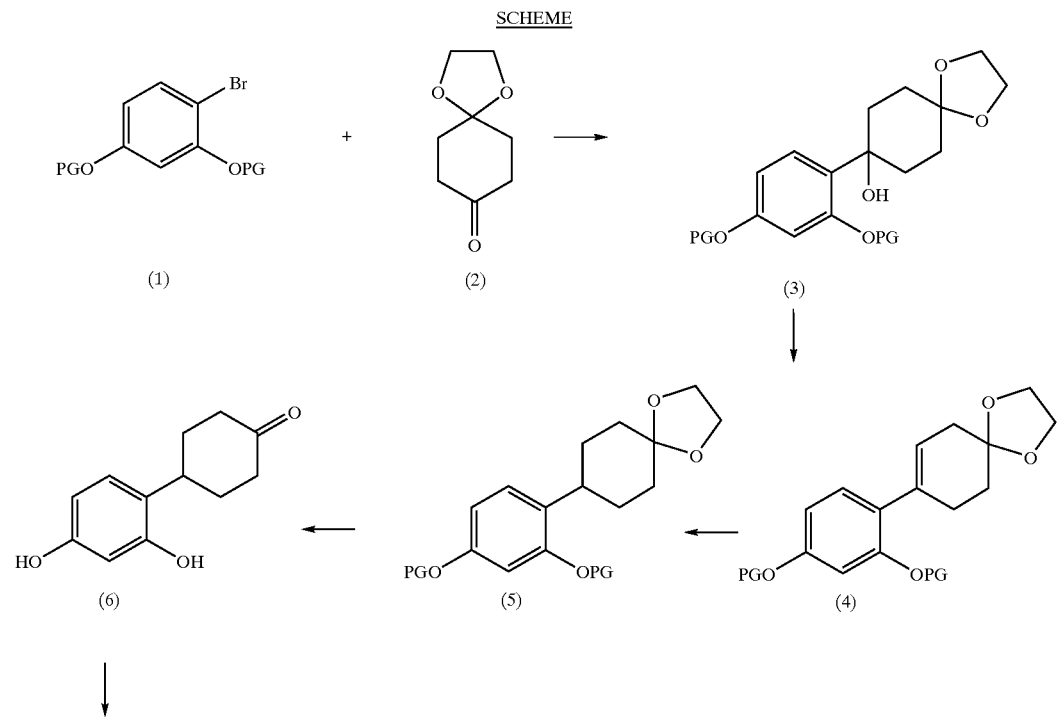

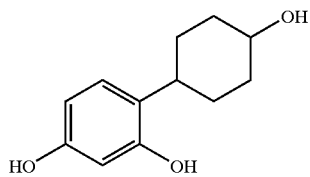

I

Referring to the scheme, compounds of formula (1) can be formed by protecting commercially available 4-bromoresorcinol. A suitable protecting group such as methoxymethyl (MOM) can be introduced by conventional methods that are well known to those skilled in the art. For example, alkylation of 4-bromoresorcinol can occur with two equivalents of methoxymethyl chloride in the presence of diisopropylamine in a halogenated solvent at about 0° C. to room temperature.

The compound of formula (2) is well known and commercially available. The compound of formula (3) can be obtained from the reaction of the compound of formula (1) with n-butyllithium in the presence of N,N,N',N'-tetramethylethylenediamine in an ethereal solvent, followed by the addition of the compound of formula (2). Dehydration of the compound of formula (3) under standard conditions, e.g., heating the compound of formula (3) at about 110° C. in a Dean-Stark apparatus in the presence of camphor sulfonic acid in a suitable solvent (e.g., toluene) yields the compound of formula (4). Hydrogenation under standard conditions, e.g., using hydrogen gas and palladium on charcoal in ethanol yields the compound of formula (5). Deprotection under suitable conditions yields the resorcinol of formula (6). The compound of formula (6) can be further derivatised under standard conditions well known to those skilled in the art to yield the resorcinol derivative of formula I. For example, reduction of the compound of formula (6) with a reducing agent such as sodium borohydride in a suitable solvent such as ethanol at a temperature between 0° C. and room temperature yields the compound of formula I.

The resorcinol derivative of formula I can alternatively be synthesized using the synthetic process described in European application EP 1 134 207 A1, by Pfizer Products Inc., which published Sep. 19, 2001, and which is incorporated herein by reference.

The compound of formula I is weakly acidic in nature and capable of forming base salts with various pharmaceutically acceptable cations. Examples of such salts include the alkali metal and alkaline earth metal salts and, particularly, the sodium and potassium salts. These salts can be prepared by conventional techniques. The chemical bases that are used as reagents to prepare the pharmaceutically acceptable base salts of this invention are those that form non-toxic base salts with the compound of formula I. Such non-toxic base salts include those derived from such pharmaceutically acceptable cations as sodium, potassium, calcium and magnesium, etc. These salts can easily be prepared by treating the corresponding acidic compound with an aqueous solution containing the desired pharmaceutically acceptable cations, and then evaporating the resulting solution to dryness, preferably under reduced pressure. Alternatively, they may also be prepared by mixing lower alkanolic solutions of the acidic compound and the desired alkali metal alkoxide together, and then evaporating the resulting solution to dryness. In either case, stoichiometric quantities of reagents are preferably employed in order to ensure completeness of reaction and maximum yields of the desired final product.

The compound of formula I and its pharmaceutically acceptable salts (hereinafter "the active compound" or "active compounds" used in this invention) are useful in the treatment of disorders of human pigmentation, including solar and simple lentigines (including age/liver spots), melasma/chloasma and post-inflammatory hyperpigmentation. The active compounds used in this invention reduce skin melanin levels by inhibiting the production of melanin, whether the latter is produced constitutively or in response to UV irradiation (such as sun exposure). Thus, the active compounds used in this invention can be used to reduce skin melanin content in non-pathological states so as to induce a lighter skin tone, as desired by the user, or to prevent melanin accumulation in skin that, e.g., has been exposed to UV irradiation. Thus, the active compounds used in this invention can be used simply to lighten skin where no pathological or disease condition exists. The active compounds used in this invention can also be used for cosmetic purposes. As used herein to refer to the depigmentation aspect of the invention, the term "a human in need of said treatment" refers to a human who, for any reason, whether medical or cosmetic, desires to reduce the melanin content of his or her skin or to prevent the melanization of the skin on any portion of his or her body.

The active compounds of this invention can be prepared as cosmetics, quasi-drugs (where applicable), or pharmaceutical drugs. As cosmetics, the active compounds of the present invention are useful in improving overall skin tone and texture.

The active compounds of this invention can appropriately be combined with other components. Examples of such components include oily components such as hydrocarbons, fats and oils such as liquid paraffin, squalene, vaseline, cetyl alcohol, isostearyl alcohol, cetyl-2-ethylhexanoate, 2-octyldodecyl alcohol, glycerin triiostearate, nut oils, and lanolin, as well as wax, silicone, surfactants, thickeners, neutralizers, antiseptics, germicides, anti-oxidants, powder components, pigments, perfumes, ultraviolet light absorbents, drugs, metallic sealant, and pH modifiers. Thus, cosmetics, quasi-drugs (where applicable), and pharmaceutical drugs of the present invention can be prepared using dermatologically, cosmetically or pharmaceutically acceptable carriers as appropriate, and as known in the art.

Occurrences in the skin or hair of noticeable but undesired pigmentation as a result of melanin production or overproduction can be treated or prevented using the methods of the present invention. Cosmetic applications for methods of the present invention include the topical application of compositions containing one or more of the compounds of the present invention to enhance or otherwise alter the visual appearance of skin or hair. The cosmetic compositions of the present invention are also useful to provide a smoother or softer skin appearance or texture.

The active compounds used in this invention can also be used in combination with skin peeling agents (including glycolic acid or trichloroacetic acid face peels) to lighten skin tone and prevent repigmentation. The appropriate dose regimen, the amount of each dose administered, and specific intervals between doses of the active compound will depend upon the particular active compound employed, the condition of the patient being treated, and the nature and severity of the disorder or condition being treated. Preferably, the active compound is administered in an amount and at an interval that results in the desired treatment of or improvement in the disorder or condition being treated.

An active compound used in this invention can also be used in combination with sun screens (UVA or UVB blockers) to prevent repigmentation, to protect against sun or UV-induced skin darkening or to enhance their ability to reduce skin melanin and their skin bleaching action. An active compound used in this invention can also be used in combination with retinoic acid or its derivatives or any compounds that interact with retinoic acid receptors and accelerate or enhance the invention's ability to reduce skin melanin and skin bleaching action, or enhance the invention's ability to prevent the accumulation of skin melanin. An active compound used in this invention can also be used in combination with 4-hydroxyanisole.

An active compound used in this invention can also be used in combination with ascorbic acid, its derivatives and ascorbic-acid based products (such as magnesium ascorbate) or other products with an anti-oxidant mechanism (such as resveratrol), which accelerate or enhance their ability to reduce skin melanin and their skin bleaching action.

As one skilled in the art would know in view of this disclosure, an active compound used according to the methods of the present invention may be used alone or in combination with other compounds known in the art to affect melanin synthesis, particularly other melanin synthesis inhibitors, including tyrosinase inhibitors. Such inhibitors include those currently known in the art and those to be developed in the future. Known inhibitors include various resorcinol derivatives, kojic acid derivatives, hydroquinone, melamine, and various types of plant extracts, among others. For example, any of the active compounds used according to a skin-lightening method of the present invention may be used in combination with a tyrosinase inhibitor or other skin-whitening agent, including any one or more of those agents, including compounds or extracts, described in the following patent publications: U.S. Pat. No. 4,278,656 to Nagai et al, issued Jul. 14, 1981, describing the use of kojic acid and its derivatives; U.S. Pat. No. 4,369,174 to Nagai et al., issued Jan. 18, 1983, describing the use of kojic acid and its derivatives; U.S. Pat. No. 4,959,393 to Torihara et al., issued Sep. 25, 1990, describing the use of 4-n-butylresorcinol, 4-isoamyl resorcinol and other resorcinol derivatives; U.S. Pat. No. 5,580,549 to Fukuda et al., issued Dec. 3, 1996, describing the use of various hydroxybenzoic acid derivatives; U.S. Pat. No. 6,123,959 to Jones et al., issued Sep. 26, 2000, describing the use of liposomes containing combinations of competitive inhibitors, such as arbutin, and non-competitive inhibitors, such as aloesin, of melanin synthesis; U.S. Pat. No. 6,132,740 to Hu, issued Oct. 17, 2000, describing the use of various resorcinol derivatives; U.S. Pat. No. 6,159,482 to Tuloup et al., issued Dec. 12, 2000, describing the use of various hydroxyphenyl oxamate derivatives; WO 99/32077 by L'Oreal, published Jul. 1, 1999, describing the use of various phenolic amides; WO 99/64025 by Fytokem Prod. Inc., published Dec. 16, 1999, describing the use of various dicotyledonous plant extracts; WO 00/56702 by Pfizer Inc., published Sep. 28, 2000 describing various resorcinol derivatives; WO 00/76473 by Shiseido Co. Ltd., published Dec. 12, 2000, describing the use of Withania plant extracts; EP 997140 by L'Oreal SA, published May 3, 2000, describing the use of combinations of mulberry and skullcap extracts with salicylic acid derivatives; JP 5221846 by Kunimasa Tomoji, published Aug. 31, 1993, describing the use of kojic acid derivatives; JP 7242687 by Shiseido Co. Ltd., published Sep. 19, 1995, describing the use of *Trichoderma* extracts; JP 7324023 by Itogawa H, published Dec. 12, 1995, describing the use of *Pseudostellariae* radix extracts; JP 8012552 by Shiseido Co. Ltd., published Jan. 16, 1996, describing the use of Amor seco extracts; JP 8012554 by Shiseido Co. Ltd., published Jan. 16, 1996, describing the use of Jabonciilo extracts; JP 8012557 by Shiseido Co. Ltd., published Jan. 16, 1996, describing the use of Huaca extracts; JP 8012560 by Shiseido Co. Ltd., published Jan. 16, 1996, describing the use of Copaiba extracts; JP 8012561 by Shiseido Co. Ltd., published Jan. 16, 1996, describing the use of *Arnica* extracts; JP 8134090 by Fujisawa, published May 28, 1996, describing the use of galactosyl-kojic acid derivatives; JP 8168378 by Kirinjo KK, published Jul. 2, 1996, describing the use of lees from rice wine production; JP 8277225 by Kansai Koso KK, published Oct. 22, 1996, describing the use of *Autocarpus incisus* extracts; JP 9002967 by Sanki Shoji KK, published Jan. 7, 1997, describing the use of *Prunus domesticus* extracts; JP 9295927 by Yagi Akira, published Nov. 18, 1997, describing the use of *Aloe vera* extracts; JP 10072330 by Kansai Kouso, published Mar. 17, 1998, describing the use of oxydesberatrol derivatives; JP 10081626 by Kamiyama KK, published Mar. 31, 1998, describing the use of 4-substituted benzoic acids; JP 10101543 by Kansai Kouso KK, published Apr. 21, 1998, describing the use of flavonoids; JP 11071231 by Maruzen Pharm., published Mar. 16, 1999, describing the use of bakuchiol; JP 11079934 by Kyodo Nyugyo, published Mar. 23, 1999, describing the use of low molecular weight thiol from sake lees; JP 11246347 by Shiseido Co. Ltd., published Sep. 14, 1999, describing the use of *Achillea millefolium* extracts; JP 11246344 by Shiseido Co. Ltd., published Sep. 14, 1999, describing the use of *Gliricidia* extracts; JP 2000-080023 by Kanebo Ltd., published Mar. 21, 2000, describing the use of metallothionine inducers; JP 2000-095663 by Kose KK, published Apr. 4, 2000, describing the use of various plant extracts; JP 2000-159681 by Hai Tai Confectionary Co. Ltd., published Jun. 13, 2000, describing the use of grape seed extract; JP-7206753 by Nikken Food KK, published Aug. 8, 1995, describing the use of dihydroxycurcumin derivatives; JP-5320025 by Kunimasa T, published Dec. 3, 1993, describing the use of kojic acid derivatives; and JP-59157009 by Yakurigaku Chuou KE, published Sep. 6, 1984, describing the use of β-thujaplicin, hydroquinone or a pyrone compound in combination with a melanin adsorbent; among others; which patent publications are incorporated herein by reference in their entireties.

This invention relates both to methods of lightening or reducing the pigmentation of skin in which an active compound used in this invention, and one or more of the other active ingredients, such as those referred to above, are administered together as part of the same pharmaceutical composition, as well as methods in which they are administered separately as part of an appropriate dose regimen designed to obtain the benefits of the combination therapy. The appropriate dose regimen, the amount of each dose administered, and specific intervals between doses of each active agent will depend upon the specific combination of active agents employed, the condition of the patient being treated, and the nature and severity of the disorder or condition being treated. Such additional active ingredients will generally be administered in amounts less than or equal to those for which they are effective as single topical therapeutic agents. The FDA approved dosages for such active agents that have received FDA approval for administration to humans are publicly available.

An active compound of this invention will generally be administered in the form of a pharmaceutical composition comprising at least the compound of formula (I) or a pharmaceutically acceptable salt thereof, together with a pharmaceutically acceptable vehicle or diluent. Alternatively, an active compound of this invention can be administered in the form of a cosmetic composition comprising at least the compound of formula (I) or a pharmaceutically acceptable salt thereof, together with a cosmetically acceptable vehicle or diluent. Such a composition is generally formulated in a conventional manner utilizing solid or liquid vehicles or diluents as appropriate for topical administration, in the form of solutions, gels, creams, jellies, pastes, lotions, ointments, salves, aerosols and the like.

Examples of vehicles for application of an active compound of this invention include an aqueous or water-alcohol solution, an emulsion of the oil-in-water or water-in-oil type, an emulsified gel, or a two-phase system. Preferably, the compositions according to the invention are in the form of lotions, creams, milks, gels, masks, microspheres or nanospheres, or vesicular dispersions. In the case of vesicular dispersions, the lipids of which the vesicles are made can be of the ionic or nonionic type, or a mixture thereof. Such vehicles can include suitable viscosity enhancing agents, pH adjusting agents, stabilizers, fragrances, etc., as known in the art of topical formulations.

As used herein, a "skin-lightening or pigmentation reducing amount" of the compound of formula I or pharmaceutically acceptable salt thereof or active compound of the invention, or an amount of a compound of formula I or pharmaceutically acceptable salt thereof or active compound of the invention, "that is effective in lightening skin", and the like, means an amount or concentration of such compound capable of detectably lightening skin or reducing pigmentation in a human after a standard or prescribed course of treatment, as determined by any standard assay.

As used herein, a "tyrosinase-inhibiting effective amount" of the compound of formula I or pharmaceutically acceptable salt thereof or active compound of the invention, and the like, means an amount or concentration of such compound capable of detectably inhibiting tyrosinase activity in a human after a standard or prescribed course of treatment, as determined by any standard assay.

As used herein, an "amount of the compound" of formula I or pharmaceutically acceptable salt thereof or active compound of the invention, and the like, capable of treating an inflammatory disorder such as psoriasis, dermatitis or acne, or treating dandruff" means an amount or concentration of such compound capable of detectably ameliorating, reducing, eliminating, slowing, or preventing the progression of, any symptom or condition associated with or caused by such disorder or condition, in a human after a standard or prescribed course of treatment, as determined by any standard assay.

An effective dosage and treatment protocol can be determined by conventional means, starting with a low dose in laboratory animals and then increasing the dosage while monitoring the effects, and systematically varying the dosage regimen as well. Animal studies, preferably mammalian studies, are commonly used to determine the maximal tolerable dose, or MTD, of a bioactive agent per kilogram weight. Those skilled in the art can extrapolate doses for efficacy and avoidance of toxicity to other species, including humans.

Before human studies of efficacy are undertaken, Phase I clinical studies in normal subjects can help establish safe doses. Numerous factors can be taken into consideration by a clinician when determining an optimal dosage for a given subject. Primary among these is the toxicity and half-life of the chosen compound. Additional factors include the size of the patient, the age of the patient, the general condition of the patient, the particular disease, condition, or disorder being treated, the severity of the disease, condition, or disorder being treated, the presence of other drugs in the patient, the effect desired, and the like. The trial dosages would be chosen after consideration of the results of animal studies and the clinical literature.

One of ordinary skill in the art will appreciate that the endpoint of treatment chosen in a particular case will vary according to the disease, condition, or disorder being treated, the outcome desired by the patient, subject, or treating physician, and other factors. Where the composition is being used to lighten skin color such as, for example, to reverse hyperpigmentation caused by, for example, inflammation or diseases such as melasma, or to lighten hair color, any one of a number of endpoints can be chosen. For example, endpoints can be defined subjectively such as, for example, when the subject is simply "satisfied" with the results of the treatment. For pharmacological compositions, the endpoint can be determined by the patient's, or the treating physician's, satisfaction with the results of the treatment. Alternatively, endpoints can be defined objectively. For example, the patient's or subject's skin or hair in the treated area can be compared to a color chart. Treatment is terminated when the color of the skin or hair in the treated area is similar in appearance to a color on the chart. Alternatively, the reflectance of the treated skin or hair can be measured, and treatment can be terminated when the treated skin or hair attains a specified reflectance. Alternatively, the melanin content of the treated hair or skin can be measured. Treatment can be terminated when the melanin content of the treated hair or skin reaches a specified value. Melanin content can be determined in any way known to the art, including by histological methods, with or without enhancement by stains for melanin.

In the depigmenting compositions according to the present invention, the concentration of the active compound of the invention is generally between 0.01 and 10%, preferably between 0.1 and 10%, relative to the total weight of the composition.

The compositions of this invention can optionally also contain a moistener, a surfactant, keratolytic, an anti-inflammatory agent, a complexing agent, an antioxidant, a preservative, a colorant, a fragrance, a pH stabilizer, a viscosity enhancing agent, or a sunscreen, or a combination thereof.

The composition of the present invention can be applied directly to the skin. Alternatively, it can be delivered by various transdermal drug delivery systems, such as transdermal patches as known in the art. For example, for topical administration, the active compound can be formulated in a solution, gel, lotion, ointment, cream, suspension, paste, liniment, powder, tincture, aerosol, patch, or the like in a pharmaceutically or cosmetically acceptable form by methods well known in the art. The composition can be any of a variety of forms common in the pharmaceutical or cosmetic arts for topical application to animals or humans, including solutions, lotions, sprays, creams, ointments, salves, gels, etc., as described below. Preferred agents are those that are viscous enough to remain on the treated area, those that do not readily evaporate, and/or those that are easily removed by rinsing with water, optionally with the aid of soaps, cleansers and/or shampoos. Actual methods for preparing topical formulations are known or apparent to those skilled in the art, and are described in detail in *Remington's Pharmaceutical Sciences*, 1990 (supra); and *Pharmaceutical Dosage Forms and Drug Delivery Systems*, 6th ed., Williams & Wilkins (1995).

In order to enhance the percutaneous absorption of the active ingredients, one or more of a number of agents can be added in the topical formulations including, but not limited to, dimethylsulfoxide, dimethylacetamide, dimethylformamide, surfactants, azone, alcohol, acetone, propylene glycol and polyethylene glycol. In addition, physical methods can also be used to enhance transdermal penetration such as, e.g., by iontophoresis or sonophoresis. Alternatively, or in addition, liposomes may be employed.

A topically applied composition of the invention contains a pharmaceutically effective amount of an active compound that lightens skin as described herein, and those ingredients as are necessary for use as a carrier, such as an emulsion, a cream, an ointment, an aqueous solution, a lotion or an aerosol. Non-limiting examples of such carriers are described in more detail below and may be found in International Patent Publication WO 00/62742, published Oct. 26, 2000; U.S. Pat. No. 5,691,380 to Mason et al., issued Nov. 25, 1997; U.S. Pat. No. 5,968,528 to Deckner et al., issued Oct. 19, 1999; U.S. Pat. No. 4,139,619 to Chidsey, III, issued Feb. 13, 1979; and U.S. Pat. No. 4,684,635 to Orentreich et al., issued Aug. 4, 1987; which are incorporated herein by reference. Suitable pharmaceutical carriers are further described in *Remington's Pharmaceutical Sciences*, 17th ed., Mack Publishing Company, Easton, Pa. (1990), which is a standard reference text in this field.

The pharmaceutical compositions of the invention may optionally include components suitable for application to keratinous tissue, that is, when incorporated into the composition, they are suitable for use in contact with human keratinous tissue without undue toxicity, incompatibility, instability, allergic response, and the like within the scope of sound medical judgment. In addition, such optional components are useful provided that they do not unacceptably alter the benefits of the active compounds of the invention. The *CTFA Cosmetic Ingredient Handbook*, Second Edition (1992) describes a wide variety of non-limiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, anti-foaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin and bisabolol and dipotassium glycyrrhizinate), skin treating agents, thickeners, and vitamins and derivatives thereof.

In addition to the skin-lightening effective amount of an active compound disclosed herein, the topical compositions of the present invention also comprise a dermatologically acceptable carrier. The phrase "dermatologically acceptable carrier", as used herein, means that the carrier is suitable for topical application to the skin, i.e., keratinous tissue, has good aesthetic properties, is compatible with the active agents of the present invention and any other components, and will not cause any safety or toxicity concerns. A safe and effective amount of carrier is from about 50% to about 99.99%, preferably from about 80% to about 99.9%, more preferably from about 90% to about 98%, and most preferably from about 90% to about 95% by weight of the composition.

The carrier utilized in the compositions of the invention can be in a wide variety of forms. These include emulsion carriers, including, but not limited to, oil-in-water, water-in-oil, water-in-oil-in-water, and oil-in-water-in-silicone emulsions, a cream, an ointment, an aqueous solution, a lotion or an aerosol. As will be understood by the skilled artisan, a given component will distribute primarily into either the water or oil/silicone phase, depending on the water solubility/dispersibility of the component in the composition.

Emulsions according to the present invention preferably contain a skin-lightening effective amount of an active compound disclosed herein and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are described in, for example, U.S. Pat. No. 3,755,560 to Dickert et al., issued Aug. 28, 1973; U.S. Pat. No. 4,421,769 to Dixon, et al., issued Dec. 20, 1983; and McCutcheon's Detergents and Emulsifiers, North American Edition, pages 317–324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, most preferably about 5 centistokes or less. The emulsion may also contain an anti-foaming agent to minimize foaming upon application to the keratinous tissue. Anti-foaming agents include high molecular weight silicones and other materials well known in the art for such use.

One type of emulsion is a water-in-silicone emulsion. Water-in-silicone emulsions contain a continuous silicone phase and a dispersed aqueous phase. Preferred water-in-silicone emulsions of the present invention comprise from about 1% to about 60%, preferably from about 5% to about 40%, more preferably from about 10% to about 20%, of a continuous silicone phase. The continuous silicone phase exists as an external phase that contains or surrounds the discontinuous aqueous phase described hereinafter.

The continuous silicone phase may contain a polyorganosiloxane oil. A preferred water-in-silicone emulsion system is formulated to provide an oxidatively stable vehicle for delivery of a skin-lightening effective amount of an agent disclosed herein. The continuous silicone phase of these preferred emulsions comprises between about 50% and about 99.9% of organopolysiloxane oil and less than about 50% of a non-silicone oil. In an especially preferred embodiment, the continuous silicone phase comprises at least about 50%, preferably from about 60% to about 99.9%, more preferably from about 70% to about 99.9%, and even more preferably from about 80% to about 99.9%, polyorganosiloxane oil of the continuous silicone phase, and up to about 50% non-silicone oils, preferably less than about 40%, more preferably less than about 30%, even more preferably less than about 10%, and most preferably less than about 2%, of the continuous silicone phase. These useful emulsion systems may provide more oxidative stability over extended periods of time than comparable water-in-oil emulsions containing lower concentrations of the polyorganosiloxane oil. Concentrations of non-silicone oils in the continuous silicone phase are minimized or avoided altogether so as to possibly further enhance oxidative stability of the active compound of the invention in the compositions. Water-in-silicone emulsions of this type are described in U.S. Pat. No. 5,691,380 to Mason et al., issued Nov. 25, 1997.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100 degrees Celsius. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes, which are known to those skilled in the art and commercially available.

The continuous silicone phase may contain one or more non-silicone oils. Concentrations of non-silicone oils in the continuous silicone phase are preferably minimized or avoided altogether so as to further enhance oxidative stability of the pharmaceutically effective agent in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g. mineral oil, vegetable oils, synthetic oils, semisynthetic oils, etc.

Useful topical compositions of the present invention comprise from about 30% to about 90%, more preferably from about 50% to about 85%, and most preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore. The aqueous phase can be water, or a combination of water and one or more water soluble or dispersible ingredients. Non-limiting examples of such optional ingredients include thickeners, acids, bases, salts, chelants, gums, water-soluble or dispersible alcohols and polyols, buffers, preservatives, sunscreening agents, colorings, and the like.

The topical compositions of the present invention typically comprise from about 25% to about 90%, preferably from about 40% to about 80%, more preferably from about 60% to about 80%, water in the dispersed aqueous phase of the composition.

The water-in-silicone emulsions of the present invention preferably comprise an emulsifier. In a preferred embodiment, the composition contains from about 0.1% to about 10% emulsifier, more preferably from about 0.5% to about 7.5%, most preferably from about 1% to about 5%, emulsifier of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with essential components of the composition, and provides the desired dispersion characteristics. Suitable emulsifiers include silicone emulsifiers, e.g., organically modified organopolysiloxanes, also known to those skilled in the art as silicone surfactants, non-silicon-containing emulsifiers, and mixtures thereof, known by those skilled in the art for use in topical personal care products.

Useful emulsifiers include a wide variety of silicone emulsifiers. These silicone emulsifiers are typically organically modified organopolysiloxanes, also known to those skilled in the art as silicone surfactants. Suitable emulsifiers are described, for example, in McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

Other preferred topical carriers include oil-in-water emulsions, having a continuous aqueous phase and a hydrophobic, water-insoluble phase ("oil phase") dispersed therein. Examples of suitable carriers comprising oil-in-water emulsions are described in U.S. Pat. No. 5,073,371 to Turner et al., issued Dec. 17, 1991; and U.S. Pat. No. 5,073,372, to Turner et al., issued Dec. 17, 1991. An especially preferred oil-in-water emulsion, containing a structuring agent, hydrophilic surfactant and water, is described in detail hereinafter.

A preferred oil-in-water emulsion comprises a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions of this invention comprise from about 0.5% to about 20%, more preferably from about 1% to about 10%, most preferably from about 1% to about 5%, of the composition, of a structuring agent. The preferred structuring agents of the present invention are selected from the group consisting of stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

The preferred oil-in-water emulsions comprise from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water. Suitable surfactants include any of a wide variety of known cationic, anionic, zwitterionic, and amphoteric surfactants. See McCutcheon's. Detergents and Emulsifiers (1986), supra; U.S. Pat. No. 5,011,681 to Ciotti et al, issued Apr. 30, 1991; U.S. Pat. No. 4,421,769 to Dixon et al. issued Dec. 20, 1983; and U.S. Pat. No. 3,755,560 to Dickert et al., issued Aug. 28, 1973. The exact surfactant chosen depends upon the pH of the composition and the other components present. Preferred are cationic surfactants, especially dialkyl quaternary ammonium compounds, examples of which are described in U.S. Pat. No. 5,151,209 to McCall et al. issued Sep. 29, 1992; U.S. Pat. No. 5,151,210 to Steuri et al. issued Sep. 29, 1992; U.S. Pat. No. 5,120,532 to Wells et al, issued Jun. 9, 1992; U.S. Pat. No. 4,387,090 to Bolich Jr., issued Jun. 7, 1983; U.S. Pat. No. 3,155,591 to Hilfer, issued Nov. 3, 1964; U.S. Pat. No. 3,929,678 to Laughlin et al, issued Dec. 30, 1975; U.S. Pat. No. 3,959,461 to Bailey et al., May 25, 1976; McCutcheon's, Detergents & Emulsifiers (North American edition 1979) M.C. Publishing Co.; and Schwartz, et al., Surface Active Agents, Their Chemistry and Technology, New York: Interscience Publishers, 1949.

Alternatively, other useful cationic emulsifiers include amino-amides. Non-limiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

A wide variety of anionic surfactants are also useful herein. See, e.g., U.S. Pat. No. 3,929,678, to Laughlin et al., issued Dec. 30, 1975. In addition, amphoteric and zwitterionic surfactants are also useful herein.

The preferred oil-in-water emulsion comprises from about 25% to about 98%, preferably from about 65% to about 95%, more preferably from about 70% to about 90% water of the topical carrier.

The hydrophobic phase is dispersed in the continuous aqueous phase. The hydrophobic phase may contain water-insoluble or partially soluble materials such as are known in the art, including but not limited to the silicones described herein in reference to silicone-in-water emulsions, and other oils and lipids such as described above in reference to emulsions.

The topical compositions of the subject invention, including but not limited to lotions and creams, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients are known and may be used herein. See, e.g., Sagarin, Cosmetics, Science and Technology, 2nd Edition, Vol. 1, pp. 3243 (1972), which contains numerous examples of materials suitable as an emollient. A preferred emollient is glycerin. Glycerin is preferably used in an amount of from or about 0.001 to or about 20%, more preferably from or about 0.01 to or about 10%, most preferably from or about 0.1 to or about 5%, e.g., 3%.

Lotions and creams according to the present invention generally comprise a solution carrier system and one or more emollients. Lotions typically comprise from about 1% to about 20%, preferably from about 5% to about 10% of emollient; from about 50% to about 90%, preferably from about 60% to about 80% water; and a skin-lightening effective amount of an agent described herein. A cream typically comprises from about 5% to about 50%, preferably from about 10% to about 20% of emollient; from about 45% to about 85%, preferably from about 50% to about 75% water; and preferably a skin-lightening effective amount of an agent described herein.

Ointments of the present invention may comprise a simple carrier base of animal or vegetable oils or semi-solid hydrocarbons (oleaginous); absorption ointment bases, which absorb water to form emulsions; or water soluble carriers, e.g., a water soluble solution carrier. Ointments may further comprise a thickening agent, such as described in Sagarin, Cosmetics, Science and Technology, 2nd Edition, Vol. 1, pp. 72–73 (1972), incorporated herein by reference, and/or an emollient. For example, an ointment may comprise from about 2% to about 10% of an emollient; from about 0.1% to about 2% of a thickening agent; and a skin-lightening effective amount of an agent described herein.

By way of non-limiting example, 1000 g of topical cream is prepared from the following types and amounts of ingredients: a skin-lightening effective amount of an active compound disclosed herein, tegacid regular (150 g) (a self-emulsifying glyceryl monostearate from Goldschmidt Chemical Corporation, New York, N.Y.), polysorbate 80 (50 g), spermaceti (100 g), propylene glycol (50 g), methylparaben (1 g), and deionized water in sufficient quantity to reach 1000 gm. The tegacid and spermaceti are melted together at a temperature of 70–80° C. The methylparaben is dissolved in about 500 g. of water and the propylene glycol, polysorbate 80, and active compound are added in turn, maintaining a temperature of 75–80° C. The methylparaben mixture is added slowly to the tegacid and spermaceti melt, with constant stirring. The addition is continued for at least 30 minutes with additional stirring until the temperature has dropped to 40–45° C. Finally, sufficient water is added to bring the final weight to 1000 g. and the preparation stirred to maintain homogeneity until cooled and congealed.

By way of non-limiting example, 1000 g of a topical ointment is prepared from the following types and amounts of ingredients: a skin-lightening effective amount of an active compound disclosed herein, zinc oxide (50 g), calamine (50 g), liquid petrolatum (heavy) (250 g), wool fat (200 g), and enough white petrolatum to reach 1000 g. Briefly, the white petrolatum and wool fat are melted and 100 g of liquid petrolatum added thereto. The skin-lightening effective amount of an active compound disclosed herein, zinc oxide, and calamine are added to the remaining liquid petrolatum and the mixture milled until the powders are finely divided and uniformly dispersed. The mixture is stirred into the white petrolatum, melted and cooled with stirring until the ointment congeals.

By way of non-limiting example, 1000 g of an ointment containing a skin-lightening effective amount of an active compound disclosed herein is prepared from the following types and amounts of ingredients: a skin-lightening effective amount of an agent disclosed herein, light liquid petrolatum (250 g), wool fat (200 g), and enough white petrolatum to reach 1000 g. Briefly, the skin-lightening effective amount of an active compound disclosed herein is finely divided and added to the light liquid petrolatum. The wool fat and white petrolatum are melted together, strained, and the temperature adjusted to 45–50° C. The liquid petrolatum slurry is added, and the ointment stirred until congealed.

By way of non-limiting example, 1000 ml of an aqueous solution containing a skin-lightening effective amount of an active compound disclosed herein is prepared from the following types and amounts of ingredients: a skin-lightening effective amount of an agent disclosed herein, polyethylene glycol 4000 (120 g) myristyl-gamma-picolinium chloride (0.2 g), polyvinylpyrrolidone (1 g), and enough deionized water to reach 1000 milliliters. Briefly, the ingredients are dissolved in the water and the resulting solution is sterilized by filtration.

By way of non-limiting example, 1000 g of lotion containing a skin-lightening effective amount of an active compound disclosed herein is prepared from the following types and amounts of ingredients: a skin-lightening effective amount of an active compound disclosed herein, N-methyl pyrolidone (40 g), and enough propylene glycol to reach 1000 g.

By way of non-limiting example, an aerosol containing a skin-lightening effective amount of an agent disclosed herein is prepared from the following types and amounts of materials: a skin-lightening effective amount of an active compound disclosed herein, absolute alcohol (4.37 g), dichlorodifluoroethane (1.43 g) and dichlorotetrafluoroethane (5.70 g). Briefly, the skin-lightening effective amount of an active compound disclosed herein is dissolved in the absolute alcohol and the resulting solution filtered to remove particles and lint. This solution is chilled to about minus 30° C. Then, to this is added the chilled mixture of dichlorodifluoromethane and dichlorotetrafluoroethane.

For oral administration, gelatin capsules or liquid-filled soft gelatin capsules can contain the active compound and powdered or liquid carriers, such as lactose, lecithin starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and to protect the tablet from the atmosphere, or enteric-coated for selective, targeted disintegration in the gastrointestinal tract. Liquid dosage forms for oral administration can contain coloring and/or flavoring to increase patient acceptance.

In general, sterile water, oil, saline, aqueous dextrose (glucose), polysorbate and related sugar solutions and glycols such as propylene glycol or polyethylene glycols, are suitable carriers for parenteral solutions. Solutions or emulsions for parenteral administration preferably contain about 5–15% polysorbate 80 or lecithin, suitable stabilizing agents and, if necessary, buffer substances. Anti-oxidizing agents such as, but not limited to, sodium bisulfite, sodium sulfite, or ascorbic acid, either alone or combined, are suitable stabilizing agents. Also useful are citric acid and its salts, and sodium EDTA. In addition, parenteral solutions can contain preservatives including, but not limited to, benzalkonium chloride, methyl- or propyl-paraben, and chlorobutanol.

Additional examples of particular formulations comprising an active compound of the present invention are provided below.

An example of the preparation of a topical gel follows.

TABLE 1

Topical Gel:

| Ingredient | Percent by Weight |
|---|---|
| Active compound | 0.50 |
| Propylene glycol | 20.00 |
| Ethanol | 20.00 |
| Carboxyvinyl polymer [Carbomer 940 ™] | 1.00 |
| Hydroxyethyl cellulose | 0.40 |
| Benzyl alcohol | 1.00 |
| Sodium hydroxide 1N | to pH 6 |
| Distilled water | Balance |

The components other than sodium hydroxide are combined to yield a homogeneous dispersion. Addition of sodium hydroxide causes the mixture to gel yielding a ready-to-use semisolid.

An example of the preparation of a topical cream follows.

TABLE 2

Topical Cream:

| Ingredient | Percent by Weight |
|---|---|
| Active compound | 0.50 |
| Stearic acid | 7.00 |
| Stearyl alcohol | 5.00 |
| Cetyl alcohol | 2.00 |
| Glycerin | 10.00 |
| Sodium laurylsulfate | 1.00 |
| Propylparaben | 0.05 |
| Methylparaben | 0.25 |
| Disodium edetate | 0.05 |
| Distilled water | Balance |

The first four ingredients are heated to approximately 70° C. to produce a uniform melt. The remaining ingredients are combined, heated to approximately 75° C., and added with mixing to the previously prepared melt. The emulsion thus formed is subsequently homogenized and cooled to yield a smooth white cream.

An example of the preparation of a topical lotion follows.

TABLE 3

Topical Lotion:

| Ingredient | Percent by Weight |
|---|---|
| Active compound | 0.50 |
| Glyceryl monostearate | 1.00 |
| Isopropyl palmitate | 4.00 |
| Polyethylene glycol 400 distearate | 2.00 |
| Glycerin | 10.00 |
| Methylparaben | 0.10 |
| Sodium cetylsulfate | 5.00 |
| Distilled water | Balance |

The first four ingredients are combined and heated to approximately 70° C., then added with agitation to a mixture of the remaining ingredients, also at about 70° C. The emulsion is appropriately homogenized and cooled to produce a smooth, white, pourable lotion.

An example of the preparation of a topical solution follows.

TABLE 4

Topical Solution:

| Ingredient | Percent by Weight |
|---|---|
| Active compound | 0.50 |
| Propylene glycol | 20.00 |
| Ethanol | 50.00 |
| Benzyl alcohol | 1.00 |
| Disodium edetate | 0.01 |
| Propyl gallate | 0.10 |
| Citric acid | 0.20 |
| Sodium hydroxide 1N | to pH 6 |
| Distilled water | Balance |

All ingredients except sodium hydroxide are combined with agitation, and the pH of the resultant solution is adjusted with 1N sodium hydroxide, to pH 6, to yield a free-flowing, quick-drying topical solution.

The topical formulations presented herein are examples of typical gel, cream, lotion, or solution dosage forms of active compounds for use in lightening skin. Other optional components can be added or excipient ratios can be adjusted to enhance cosmetic acceptability of the formulations. Additionally, these alterations can be made to customize the composition toward a particular active compound, for example, to ensure solubilization or to enhance chemical or physical stability. Optional components would include viscosity adjusters such as celluloses, emollient oils such as mineral oil or glycerides, humectants such as polyols, cosolvents such as isopropyl alcohol or acetone, emulsifying agents of the anionic, cationic and non-ionic types, preservatives, antioxidants, opacifiers, colorants and perfumes.

An example of the preparation of an oral tablet formulation follows.

TABLE 5

Tablet Formulation:

| Ingredient | Amount (mg) |
|---|---|
| Active Compound | 25 |
| Lactose | 50 |
| Cornstarch (for mix) | 10 |
| Cornstarch (paste) | 10 |
| Magnesium stearate (1%) | 5 |
| Total | 100 |

The active compound, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet.

An example of the preparation of an oral solution follows.

TABLE 6

Oral Solution:

| Ingredient | Percent by Weight |
|---|---|
| Active Compound | 2.0 |
| Ethyl alcohol | 10.0 |
| Benzyl alcohol | 1.0 |
| Peppermint flavor | 0.2 |
| Vanillin | 0.2 |
| Polysorbate 40 | 0.1 |
| Sucrose | 50.0 |
| Purified water | Balance |

The ingredients are combined and mixed to form a uniform solution.

As will be understood by those in the art, the compositions and pharmaceutical compositions of the invention may be provided as part of a kit. Kits of the present invention comprise a container comprising one or more active compounds and/or pharmaceutical compositions of the present invention that lighten skin. The container is designed to prevent contamination, minimize evaporation or drying of the composition, etc. Optionally, the kit further comprises printed instructions as a label or package insert directing the use of the enclosed compound or composition to lighten skin pigmentation. The compound or composition may or may not be provided in a preset unit dose or usage amount.

The ability of the active compounds used in this invention to inhibit tyrosinase can be determined using any of the following procedures.

1. Tyrosinase (DOPA Oxidase) Assay Using Cell Lysate:

Human melanoma cell line, SKMEL 188 (licensed from Memorial Sloan-Kettering), is used in the cell lysate assay and the screen. In the assay, compounds and L-dihydroxyphenylalanine (L-DOPA) (100 $\mu$g/ml) are incubated with the cell lysates containing human tyrosinase for 8 hr before the plates are read at 405 nm. Potency of the compounds in DOPA oxidase assay is correlated very well with that in tyrosine hydroxylase assay using $^3$H-tyrosine as a substrate. 4-(2,4-dihydroxyphenyl)cyclohexanol, when tested in this assay, exhibited an $IC_{50}$ of 0.2$\mu$M.

2. Melanin Assay in Human Primary Melanocytes:

Compounds are incubated with human primary melanocytes in the presence of α-melanocyte stimulating hormone (α-MSH) for 2–3 days. Cells are then lysed with sodium hydroxide and sodium dodecyl sulfate (SDS) and melanin signals are read at 405 nm. Alternatively, $^{14}$C-DOPA is added to the cells in combination with tyrosinase inhibitors and acid-insoluble $^{14}$C-melanin is quantitated by a scintillation counter. $IC_{50}$ reflects the inhibitory potency of the compound in the new melanin synthesis that was stimulated by α-MSH.

3. Tyrosine Kinase Assay (TK):

TK assays can be performed using purified tyrosine kinases domain of c-met, erb-B2, or IGF-r. A specific antibody against phosphorylated tyrosine residue is used in the assay. Colorimetric signals are generated by horseradish peroxidase, which is conjugated to the antibody.

4. Human Skin Equivalent Model:

A mixture of human melanocytes and keratinocytes is grown in an air-liquid interphase. This tissue culture forms a three dimensional structure that histologically and microscopically resembles the human skin epidermis. A test compound is added on top of the cells to mimic topical drug application. After incubation with the compounds (10 $\mu$M) for 3 days, the cells are washed extensively and lysed for DOPA oxidase assay.

5. IL-1 Assay (Interleukin-1 Assay):

An IL-1α ELISA assay (R&D system) can be used to evaluate the effect of the compound on IL-1 secretion in a human skin equivalent model. IL-1α is a pro-inflammatory cytokine and plays a role in UV-induced skin inflammation.

6. In vivo Study:

Black or dark brown guinea pigs with homogeneous skin color can be used in this study. A solution of the test compound (5% in ethanol:propylene glycol, 70:30) and the vehicle control are applied to the animals twice daily, 5 days per week for 4–8 weeks. Using this assay, depigmentation of skin by 4-(2,4-dihydroxyphenyl)cyclohexanol was observed.

The present invention is illustrated by the following example. It will be understood, however, that the invention is not limited to the specific details of this example. Proton nuclear magnetic resonance spectra ($^1$H NMR) were measured for solutions in $d_6$-DMSO, CDCl$_3$ or $d_4$-MeOH, and peak positions are expressed in parts per million (ppm) downfield from tetramethylsilane (TMS). The peak shapes are denoted as follows: s, singlet; d, doublet; t, triplet; q, quartet, m, multiplet, b, broad.

The following example is illustrative only, and is not intended to limit the scope of the present invention.

EXAMPLES

Intermediate 1

1-3-Di(methoxymethoxy)-4-bromobenzene

An oven-dried 250 mL round-bottomed flask equipped with magnetic stirrer, under an argon atmosphere, was loaded with 4-bromoresorcinol (9.45 g, 50 mmol) and CH$_2$Cl$_2$ (50 ml). The stirred suspension was cooled to 0° C., and diisopropylamine (19.1 ml, 110 mmol) was added in one portion via syringe. Stirring of the red solution was continued for a further 10 min before methyl chloromethyl ether (10.7 ml, 120 mmol) was added dropwise via syringe ensuring the internal temperature did not exceed 10° C. The resulting yellow solution was then allowed to warm to room temperature overnight. Ammonium hydroxide solution (50 mL, 50%) was poured into the reaction vessel and stirring was continued for 1 hr. The mixture was poured into a separating funnel and the phases separated. The aqueous phase was then extracted with CH$_2$Cl$_2$ (3×30 ml), and the combined organics washed with brine (20 ml), dried over anhydrous magnesium sulphate, filtered and concentrated in vacuo affording an orange oil. Purification was achieved by flash column chromatography, (SiO$_2$, ethyl acetate/petroleum ether, 1:1, v/v), furnishing the title product (10.7 g, 77%) as a pale yellow oil. $\delta_H$(CDCl$_3$) 7.42 (1H, d), 6.88 (1H, d), 6.64 (1H, dd), 5.24 (2H, s), 5.15 (2H, s), 3.53 (3H, s), 3.48 (3H, s).

Intermediate 2

1-Hydroxy-1-(2,4-dihydroxyphenylbis(methoxymethylether))cyclohexan-4-one ethylene ketal An oven-dried 250 ml round-bottomed flask, equipped with magnetic stirrer, under an argon atmosphere, was loaded with 4-bromoresorcinol-bis(methoxymethyl) ether (2.00 g, 7.2 mmol) and THF (50 mL). N,N,N',N'-Tetramethylethylene diamine (2.3 ml, 15.2 mmol) was added in one portion via syringe and the stirred solution was cooled to −78° C. n-Butyl lithium (9.5 ml, 15.2 mmol, 1.6M in hexane) was added dropwise via syringe. The resulting yellow solution was stirred for 1 hr at −78° C., and 1,4-cyclohexanedione monoethylene ketal (1.35 g, 8.7 mmol) was added as a solution in THF (25 ml) slowly via syringe.

The resulting solution was stirred at −78° C. for 1 hr, and then allowed to warm to room temperature overnight. Hydrochloric acid (20 ml, 2M) was added and the reaction mixture stirred vigorously for 15 min. Ethyl acetate (100 ml) was added and the mixture poured into a separating funnel. The phases were separated and the aqueous phase was extracted with ethyl acetate (3×20 ml). The combined organics were washed with brine (20 ml), dried over anhydrous magnesium sulphate, filtered and concentrated affording an orange oil which was purified by flash column chromatography (SiO$_2$, ethyl acetate/petroleum ether, 45:55, v/v). The title product (1.42 g, 56%) was isolated as a colourless oil. m/z (ES$^+$) 337 (M−H$_2$O+H)$^+$; $\delta_H$(CDCl$_3$) 1.6–1.64 (2H, m), 2.00–2.18 (6H, m), 3.44 (3H, s), 3.48 (3H, s), 3.90–3.97 (4H, m), 5.111 (2H, s), 5.24 (2H, s), 6.64 (1H, dd), 6.82 (1H, d), 7.20 (1H, d).

Intermediate 3

1-(2,4-Dihydroxyphenylbis(methoxymethylether)cyclohex-1-en-4-one ethylene ketal 1-Hydroxy-1-(2,4-dihydroxyphenylbis(methoxymethylether))cyclohexane-4-one ethylene ketal (1.40 g, 3.95 mmol) was placed in a 50 ml round-bottomed flask equipped with magnetic stirrer and a Dean-Stark apparatus. Toluene (30 ml) was added, followed by camphor sulphonic acid (10 mg). The stirred solution was then heated under reflux for 1 hr, cooled, and saturated aqueous sodium bicarbonate solution (10 ml) was added. The mixture was poured into a separating funnel and the phases separated. The aqueous phase was extracted with ethyl acetate (2×15 ml), and the combined organics were washed with brine (15 ml), dried over anhydrous magnesium sulphate, filtered, and then concentrated in vacuo yielding an orange oil that was purified by flash column chromatography (SiO$_2$, ethyl acetate/petroleum ether, 45:55, v/v) to afford the title product (0.94 g) as a colourless oil. $\delta_H$(CDCl$_3$) 1.84 (2H, t), 2.41–2.43 (2H, m), 2.56–2.62 (2H, m), 3.47 (6H, s), 3.98–402 (4H, m), 5.13 (4H, s), 5.58–5.63 (1H, m), 6.64 (1H, dd), 6.78 (1H, d), 7.08 (1H, d).

Intermediate 4

1-(2,4-Dihydroxyphenylbis(methoxymethyl ether))cyclohexan-4-one ethylene ketal 1-(2,4-Dihydroxyphenylbis(methoxymethylether)cyclohex-1-en-4-one ethylene ketal (0.950 g, 2.83 mmol) and palladium (200 mg, 10% on carbon) were stirred under an atmosphere of hydrogen for 15 hr. The mixture was then filtered through a plug of Celite, washing with ethyl acetate. The filtrate was evaporated to dryness, affording the title product (0.955 g, 100%) as a colourless oil. $\delta_H$(CDCl$_3$) 1.67–1.87 (8H, m), 2.90–2.99 (1H, m), 3.46 (3H, s), 3.48 (3H, s), 3.97 (4H, s), 5.12 (2H, s), 5.18 (2H, s), 6.65 (1H, dd), 6.78 (1H, d), 7.12 (1H, d).

Intermediate 5

4-(2,4-Dihydroxyphenyl)cyclohexanone

A round-bottomed flask equipped with magnetic stirrer was loaded with 1-(2,4-dihydroxyphenylbis(methoxymethylether))cyclohexan-4-one ethylene ketal (1.30 g, 3.9 mmol) and methanol (15 ml). To the resulting stirred solution was added aqueous HCl (15 ml, 1M) in one portion. After stirring for 1 hr at room temperature, the acid was quenched by adding saturated aqueous sodium bicarbonate solution (10 ml). After stirring vigorously for 10 min, the reaction mixture was transferred to a separating funnel, the phases separated, and the aqueous phase extracted with ethyl acetate (3×20 ml). The combined organic phases were washed with brine and the solvent evaporated. To the slightly wet crude product was added methanol (30 ml) and acidic ion exchange resin (4 g). The resulting mixture was heated under reflux with stirring for 5 hr. Filtering through a plug of Celite, washing with ethyl acetate, followed by removal of solvent in vacuo, afforded an orange oil. Purification by flash column chromatography, ($SiO_2$, ethyl acetate/petroleum ether, 1:1, v/v) furnished the title product as a white powder (0.54 g, 68%). m/z (ES) 411 (2M−1); $\delta_H(CD_3OD)$ 1.94 (2H, ddd), 2.16–2.23 (2H, m), 2.41 (2H, dt), 2.62 (1H, t), 2.63 (1H, t), 6.24(1H, dd), 6.31 (1H, d)

Example 1

(anti)-4-(2,4-Dihydroxyphenyl)cyclohexanol 4-(2,4-Dihydroxyphenyl)cyclohexanone (18 mg) was placed in a 25 ml round-bottomed flask equipped with magnetic stirrer. Ethanol (5 ml) was added, followed by sodium borohydride (3.3 mg), and the reaction mixture was stirred for 16 hr. Aqueous HCl (20 ml, 1M), followed by ethyl acetate (20 ml), was added, and the organic phase removed and washed with brine (15 ml), dried over anhydrous magnesium sulphate, filtered, and then concentrated in vacuo. The residue was purified by flash column chromatography ($SiO_2$, ethyl acetate/petroleum ether, 60:40, v/v) to afford the title product (14 mg, 78%) as a white solid. m/z (ES⁻) 267 ((M+60)−1); $\delta_H(CD_3OD)$ 1.38–1.56 (4H, m), 1.85–188 (2H, m), 204–207 (2H, m), 2.80 (1H, tt), 3.58–3.65 (1H, m), 6.24–6.29 (2H, m), 6.90 (1H, d).

All patents, patent applications, and publications cited above are incorporated herein by reference in their entirety.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims.

What is claimed is:

1. A topical pharmaceutical composition for lightening skin or reducing the pigmentation of skin in a human, comprising an amount of a compound of formula I

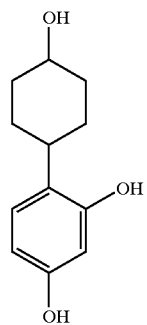

or a pharmaceutically acceptable salt thereof, which amount is effective in lightening skin or reducing the pigmentation of skin, and a pharmaceutically acceptable carrier.

2. The composition of claim 1, further comprising a sunscreen.

3. The composition of claim 1, further comprising resveratrol or another active agent that is an anti-oxidant.

4. The composition of claim 1, further comprising retinoic acid, a derivative of retinoic acid, or any compound that interacts with retinoic acid receptors and accelerates or enhances the composition's ability to reduce skin melanin and skin bleaching action.

5. The composition of claim 1, further comprising glycolic acid, trichloroacetic acid or another skin peeling agent.

6. The composition of claim 1, which is in the form of a water-alcohol solution, an oil-in-water emulsion, a water-in-oil emulsion, an emulsified gel, or a two-phase system.

7. The composition of claim 1, which is in the form of a lotion, cream, milk, gel, jelly, paste, ointment, salve, mask, microspheres, nanospheres, or a vesicular dispersion.

8. The composition of claim 1, wherein the skin-lightening or pigmentation-reducing amount of the compound of formula I or pharmaceutically acceptable salt thereof is an amount effective to inhibit tyrosinase.

9. A method of lightening skin or reducing the pigmentation of skin in a human, comprising administering to said human an amount of a compound of formula I

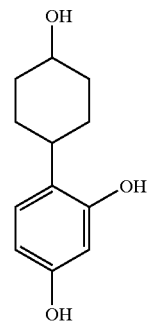

or a pharmaceutically acceptable salt thereof, which amount is effective in lightening skin or reducing the pigmentation of skin.

10. The method of claim 9, in which the compound of formula I or the pharmaceutically acceptable salt thereof is formulated in a water-alcohol solution, an oil-in-water emulsion, a water-in-oil emulsion, an emulsified gel, or a two-phase system.

11. The method of claim 9, in which the compound of formula I or the pharmaceutically acceptable salt thereof is formulated in a lotion, cream, milk, gel, jelly, paste, ointment, salve, mask, microspheres, nanospheres, or a vesicular dispersion.

12. The method of claim 9, wherein the skin-lightening or pigmentation-reducing amount of the compound of formula I or pharmaceutically acceptable salt thereof is an amount effective to inhibit tyrosinase.

13. A method of inhibiting tyrosinase in a human, comprising administering to said human a tyrosinase-inhibiting effective amount of a compound of formula I

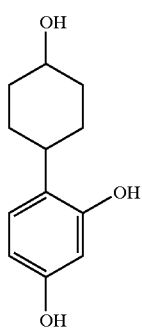

or a pharmaceutically acceptable salt thereof.

14. The method of claim 13, in which the compound of formula I or the pharmaceutically acceptable salt thereof is formulated in a water-alcohol solution, an oil-in-water emulsion, a water-in-oil emulsion, an emulsified gel, or a two-phase system.

15. The method of claim 13, in which the compound of formula I or the pharmaceutically acceptable salt thereof is formulated in a lotion, cream, milk, gel, jelly, paste, ointment, salve, mask, microspheres, nanospheres, or a vesicular dispersion.

16. A method of treating an inflammatory disorder or dandruff in a human, comprising administering to said human an amount of a compound of formula I

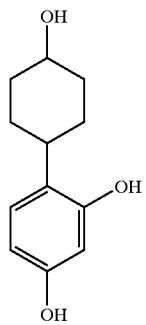

or a pharmaceutically acceptable salt thereof, which amount is effective in treating such disorder.

17. The method of claim 16, wherein the inflammatory disorder is psoriasis, dermatitis or acne.

* * * * *